(12) United States Patent
Burggraf et al.

(10) Patent No.: US 6,556,945 B1
(45) Date of Patent: Apr. 29, 2003

(54) MEASUREMENT OF GROOVES AND LONG WAVES ON RAILS WITH A LONGITUDINAL STREAK OF LIGHT

(75) Inventors: Hubert Burggraf, Oyten (DE); Rolf Kettenburg, Oyten (DE); Andreas Krupp, Langwedel (DE); Dirk Maiwald, Weyhe (DE); Dirk Rathjen, Bremen (DE)

(73) Assignee: STN Atlas Elektronik GmbH, Breman (DE)

( * ) Notice: Subject to any disclaimer, the term of this patent is extended or adjusted under 35 U.S.C. 154(b) by 0 days.

(21) Appl. No.: 09/424,543

(22) PCT Filed: May 8, 1998

(86) PCT No.: PCT/EP98/02714
§ 371 (c)(1),
(2), (4) Date: Mar. 7, 2000

(87) PCT Pub. No.: WO98/54543
PCT Pub. Date: Dec. 3, 1998

(30) Foreign Application Priority Data

May 26, 1997 (DE) .......................................... 197 21 915

(51) Int. Cl.$^7$ .............................................. G01B 11/02
(52) U.S. Cl. .................... 702/159; 356/606; 356/607; 382/108
(58) Field of Search ......................... 702/159; 356/606, 356/607; 382/108

(56) References Cited

U.S. PATENT DOCUMENTS

| | | | |
|---|---|---|---|
| 2,253,054 A | 8/1941 | Tuttle et al. .................... | 88/14 |
| 3,908,079 A * | 9/1975 | Worthley ...................... | 702/167 |
| 4,362,366 A * | 12/1982 | Gottschalk ................... | 132/116 |
| 4,425,041 A | 1/1984 | Nishiyama ................... | 365/371 |
| 4,548,070 A * | 10/1985 | Panetti ......................... | 33/1 Q |
| 4,896,964 A * | 1/1990 | Kitazume .................... | 356/602 |
| 5,140,776 A | 8/1992 | Isdahl et al. ............. | 51/165.71 |
| 5,353,512 A * | 10/1994 | Theurer et al. ............... | 33/1 Q |
| 5,465,214 A | 11/1995 | Jeuniaux et al. ............ | 364/472 |

FOREIGN PATENT DOCUMENTS

| | | | | |
|---|---|---|---|---|
| DE | 26 18 365 | | 11/1977 | ............ B61K/9/09 |
| DE | 39 13 159 A1 | | 10/1990 | ............ E01B/35/06 |
| DE | 42 37 713 A1 | | 5/1993 | ............ E01B/35/06 |
| DE | 195 35 259 A1 | | 3/1997 | ............ G01N/33/36 |
| EP | 0 433 555 A2 | | 6/1991 | ............ G01B/11/16 |

OTHER PUBLICATIONS

Leon–Garcia, Alberto. Probability and Random Processes for Electrical Engineering. 1994. Addison–Wesley Publishing Company. Second Edition. Pp. 403, 404, and 411–413.*

* cited by examiner

*Primary Examiner*—Kamini Shah
*Assistant Examiner*—Stephen J. Cherry
(74) *Attorney, Agent, or Firm*—Venable; Norman N. Kunitz

(57) ABSTRACT

A system for measuring unevenness formed by grooves and/or long waves in a surface of an object by using a measuring platform. The system moves the object and the measuring platform relative to each other and projects from the measuring platform a light streak that extends in a direction of the movement onto a surface of the object at a fixed projection angle that is tilted relative to a surface normal of the surface. The light streak is reproduced on a planar, position-sensitive photo receiver with a plurality of successive instantaneous exposures of the photo receiver, where the photo receiver is fixedly arranged on the measuring platform with a recording angle that is tilted relative to the fixed projection angle. The system records the surface along the direction of the movement with a plurality of continuous light-streak images and determines a surface profile of the surface along the direction of the movement from deformations in the plurality of the light-streak images.

23 Claims, 3 Drawing Sheets

MEASUREMENT OF GROOVES AND LONG WAVES ON RAILS WITH A LONGITUDINAL STREAK OF LIGHT

BACKGROUND OF THE INVENTION

The invention relates to a method for measuring unevenness created by grooves and/or long waves in the surface of an object from a measuring platform, wherein the measuring platform and the object are moved relative to each other.

One example for the use of such a method is the measuring of such unevenness on the driving surface of rails in a track bed, designed for rail-bound transport means, e.g. trains, street cars, subways and the like. Due to the rail traffic, unevenness occurs locally and periodically on the rail tops that form the driving surfaces. Unevenness of this type produces structure-born noise and vibrations when the wheels of the rail vehicle roll off, which can lead to noise pollution for the environment as well as noise and vibrations stress for the passengers. The unevenness in the driving surface must be recognized early on because it worsens with increased rail traffic and leads to a considerable reduction in travel comfort and also travel safety. Rails with unevenness in the driving surface are subject to considerable wear and tear and have a much shorter service life than rails without such unevenness of the driving surface. The unevenness of the driving surface, which is defined as grooves with a wave length $\lambda$ between 10 mm and 300 mm and as so-called longitudinal waves having a wave length $\lambda$ between 300 mm and 3000 mm, must be removed by grinding, milling or planing the rails. A number of measuring methods have been developed for this, which allow measuring any unevenness of the driving surface, that is to say during routine inspection drives as well as for the purpose of a subsequent testing and documentation of the rail surface treatment, which has been carried out. In the process, a so-called arithmetic average rough value $R_a$ according to DIN 4768 is defined for the normal state of the rails, which must not be exceeded over a predetermined rail length L.

According to a conventional method for measuring unevenness of this type on the driving surface of rails (Stuart L. Grassie "Measurement of railhead longitudinal profiles: a comparison of different techniques," Wear 191, (1996), pages 245–251) such as the traveling chord measuring principle, the distance between the measuring platform and a ruler that touches the rail with its two end points is measured by means of a tracer pin or a sensor that measures without contact. The ruler is pressed by the measuring platform against the rail and is moved together with the measuring platform along the rail. If the profile deviation in a vertical section through the rail surface is a planar curve, then the ruler represents a chord of this curve. The profile is determined from the measured distances, also called arrow heights, which can further be used to compute the roughness of the driving surface. In order to detect all possible wavelengths of the driving surface unevenness, several ruler lengths must be used, which results in extreme disadvantages when realizing the method. Another disadvantage of the method is that the tracer pin must be pressed against the rail, regardless of the measuring platform vibration, which requires a high mechanical expenditure. If an inertial system is attached to the car axle, the measurements are recorded in a coordinate system that is independent of the measuring platform. To be sure, the measuring method is simple, but the measuring system is described with the aid of very many parameters that must be known. The measuring system behavior depends on the speed of the measuring platform, the rail, the type of tie and the track bed material. A local measurement is not possible, but only statistical statements concerning the profile deviation over measured distances of approximately 10 m. Inertial systems furthermore are only operational with sufficient accuracy starting with a minimum speed of the measuring platform of approximately 20 km/h, thus making it impossible to use such measuring systems in connection with slow-moving machines for working the railhead.

SUMMARY OF THE INVENTION

It is therefore the object of the invention to provide a method of the aforementioned type as well as a device for use with this method, which method or device permits measurements without making contact, is rugged with respect to the relative movement between measuring platform and object and delivers uniformly good measuring results, independent of the movement speed.

This object is solved with a method for measuring unevenness formed by grooves and/or long waves in a surface of an object by using a measuring platform, including: moving an object and a measuring platform relative to each other; projecting from the measuring platform a light streak that extends in a direction of the movement onto a surface of the object at a fixed projection angle that is tilted relative to a surface normal of the surface; reproducing the light streak on a planar, position-sensitive photo receiver with a plurality of successive instantaneous exposures of the photo receiver, where the photo receiver is fixedly arranged on the measuring platform with a recording angle that is tilted relative to the fixed projection angle; recording the surface along the direction of the movement with a plurality of continuous light-streak images; and determining a surface profile of the surface along the direction of the movement from deformations in the plurality of the light-streak images.

The method according to the invention has the advantage that all unevenness in the object surface can be detected with high measuring accuracy, regardless of the wavelength. The method is continuous and fully automatic and, if used for the driving path of rail traffic means, can be used with extremely slow as well as extremely fast measuring platforms moving along the rails because it does not depend on the speed. Furthermore, it can be used without detraction either together with a working machine for smoothing the rail surface, so as to monitor and document the result of the working operation, or within the framework of inspection drives for testing the condition of the rail surface on a measuring car that is traveling at a high speed (up to 200 km/h). The method according to the invention is insensitive to changes in the distance and a tilting of the measuring platform, relative to the rails, and can thus be used without problems on measuring platforms, which are subjected to vibrations and movements during the measuring operation.

A useful embodiment of the method according to the invention or the device according to the invention for realizing said method, as well as advantageous modifications and embodiments of the invention follow in the detailed description of the invention.

The invention is described in further detail in the following with the aid of an exemplary embodiment, shown in the drawing, of a device for measuring the driving surface unevenness of rails from a measuring platform that moves along the rails.

DETAILED DESCRIPTION OF THE INVENTION

Figure 1:
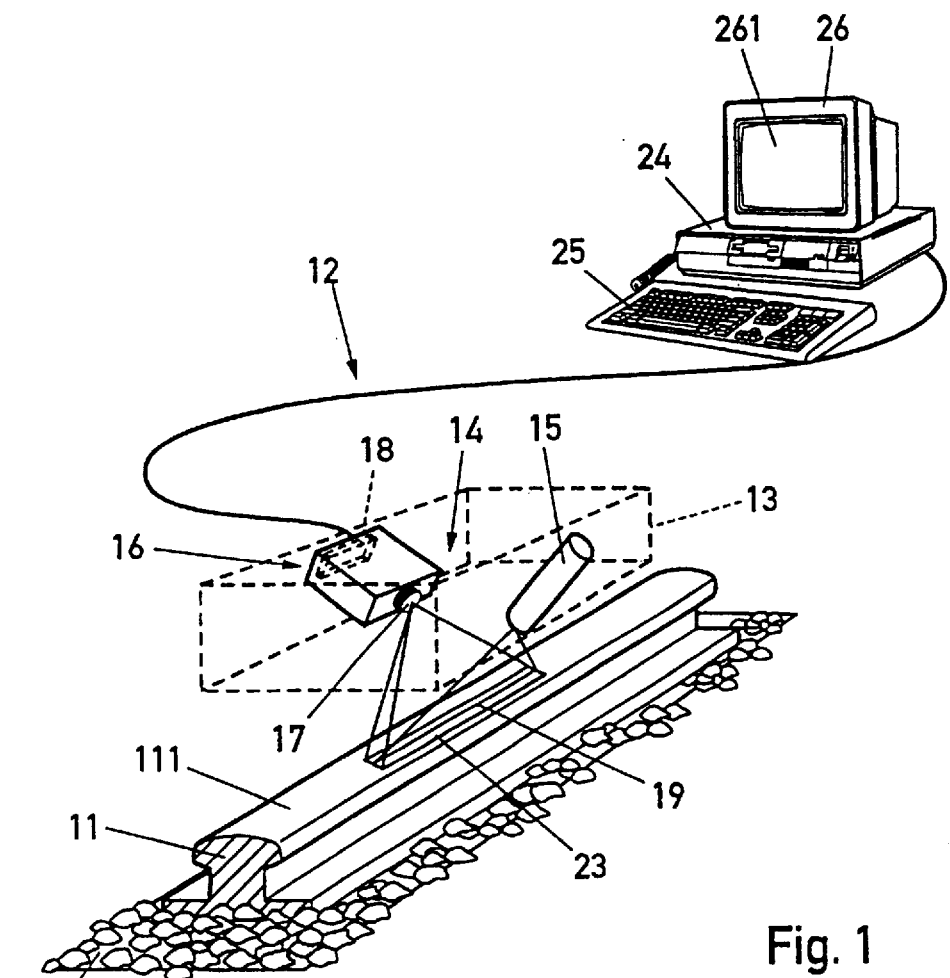
FIG. 1 is a perspective view of a measuring device for measuring the surface unevenness of rails.

Referring to FIG. 1, a track bed 10 for a rail length and a section 11 of rail line installed on the track bed 10 are shown. The top of the rail 11 forms a driving surface 111 for the wheels of a rail vehicle. Unevenness develops on this driving surface 111 as a result of driving operations, and are so-called as grooves or long waves, where they have different wavelengths. Grooves are uneven sections having a wavelength $\lambda$ of between 10 mm and 300 mm, while long waves are uneven sections having a wavelength $\lambda$ of 300 mm to 3000 mm. For a regular driving operation, it is necessary to remove the unevenness sufficiently early through grinding, milling or planing of the driving surface 111. Any unevenness of the driving surface is measured by means of a measuring device 12, so as to monitor the result of work on the rails or to determine during an inspection whether the rails need to be treated. The measuring device 12 is installed on a measuring platform 13 for this, which is driven along the rail 11 with any optional speed. The measuring platform 13 with the measuring device 12 may be installed on the underside of a driven or pulled measuring car to perform inspection and the measuring car may be. driven over the rail lines at a speed of up to 200 km per hour. Furthermore, the measuring platform maybe coupled with a grinding, milling or planing machine that moves along the tracks at an extremely low speed, for the purpose of monitoring and documenting the results of the rail treatment.

Figure 2:
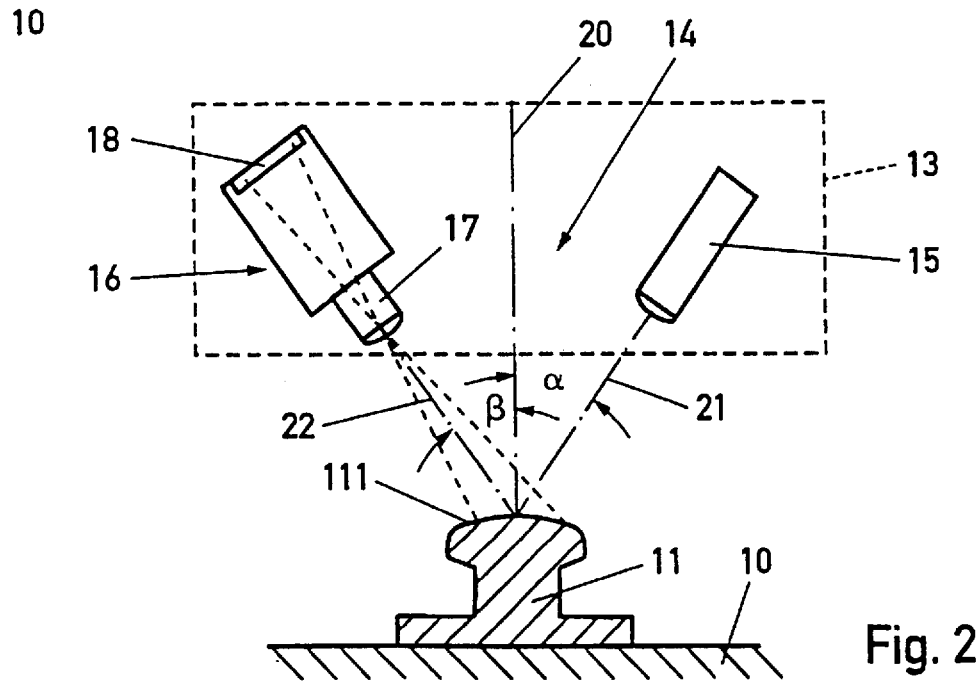
FIG. 2 is a cross sectional view of the measuring device in FIG. 1.

FIG. 1 is a perspective view of the measuring device 12 and FIG. 2 is a frontal view of the measuring device. The measuring device is provided with a so-called light-section or laser triangulation system 14, comprising a laser light source 15 with line optics and a camera 16 with camera lens 17, as well as a position-sensitive photo receiver 18. The laser-light source 15 with line optics projects a laser streak or light streak 19 of limited length (approximately 300 mm for the exemplary embodiment) in a longitudinal rail direction onto the driving surface 111. The laser light source 15 with line optics is arranged on the measuring platform 13 in such a way that the projection angle is tilted relative to a rail normal 20. In FIG. 2, the projection angle is referred to as α. An optical axis 21 for the line optics of the laser light source 15 and an optical axis 22 of the camera lens 17 of the camera 16 are shown. As can be seen therein, the optical axis 22 of camera lens 17 is tilted relative to the optical axis 21 of the laser light source 15 with line optics, wherein the angle between the optical axis 22 and the rail normal 20 is β. The section image received by the camera 16 and projected onto the photo receiver 18 covers the driving surface 111 over the length of the light streak 19. The camera lens 17 of the camera 16 has an anamorphotic design and is oriented such that the linear magnification in longitudinal direction of the rail 11 is smaller than the linear magnification lateral thereto, meaning across the driving surface 111. An anamorphotic camera lens of this type can be realized with a system of lenses, comprising cylindrical lenses such as intersecting or specially ground ellipsoid lenses. Camera lenses with anamorphotic image formation are normally available commercially for linear magnification ratios between horizontal and vertical image up to a factor of 2. In the exemplary embodiment described herein, an anamorphotic image-forming camera lens 17 with linear magnification difference having a factor higher than 15 is used. With this, it is possible to form an image of the light streak 19, projected onto the driving surface 111, over its total length of up to 500 mm and to project the contour of the line in lateral rail direction for an object size range of less than 40 mm onto the photo receiver 18, e.g. designed as CCD chip. It means that for a photo receiver 18 with 500×500 pixel, for example, for which the light streak 19 is projected in longitudinal rail direction, e.g. along a CCD line, an illuminated pixel permits a local resolution of 1 mm in the longitudinal direction while an illuminated pixel in a column of the light streak 19 image in the lateral direction of the rail corresponds to a local resolution of 80 $\mu$m.

The camera 16 is connected on the output side to a PC 24 with a keyboard 25 and a monitor 26, which is used to process the output signals from the camera 16. The result of the unevenness measurement is displayed on the screen 261 of the monitor 26 and can be documented additionally by means of a printer or plotter. During the drive of the measuring cart with the measuring platform 13, the light streak 19 that is moved along the rail 11 is scanned with the camera 16 with a picture-taking sequence that is synchronized with the driving speed of the measuring platform 13. In the exemplary embodiment, the picture-taking sequence or frame rate is approximately 50 Hz for a driving speed of approximately 50 km/h and 200 Hz for a driving speed of approximately 200 km/h. The driving surface 111 of the rail 11 is scanned continuously in the longitudinal rail direction by the instantaneous exposures of the camera 16, so that the light streak images obtained by the individual instantaneous exposures continuously record the driving surface 111 in the longitudinal rail direction. An overlapping technique is preferably used, where the sequential light streak images record overlapping longitudinal sections of the rails. When the driving surface 111 is uneven, the images of light streak 19 that are recorded by the camera 16 are deformed, wherein the contour course of the light streak image is a measure of the unevenness in the driving surface 111 in the longitudinal direction of the rail 11. From a suitable signal processing by the PC 24, the surface profile of the driving surface 111 along the rail 11 is determined based on deformations in the light streak images.

The picture-taking sequence or frame rate of the camera 16, which is synchronized with the driving speed of the measuring platform 13, can be achieved in two ways. In the first method, a continuously emitting laser light source 14 is used and the opening sides of a shutter for the camera 16 are synchronized with the driving speed of the measuring platform 13. In the second method, a pulsed laser light source 14 is used and the emission frequency of the light pulses is synchronized with the driving speed of measuring platform 13. The shutter of camera 16 can either be omitted or remain open continuously.

In order to synchronize the picture taking sequence with the driving speed of a measuring cart, the measuring cart is provided (not shown in the drawings) with an angular momentum transmitter 27 (FIG. 3), which supplies a specific number of pulses for each wheel rotation of the measuring cart. With a known wheel diameter, the scanning interval can be calculated easily, as well as the time interval between the successive instantaneous exposures of the camera 16. A synchronizing device 28 (FIG. 3) ensures that the camera 16 takes pictures at the points in time at which the measuring platform 13 has moved forward by one scanning interval. In place of the angular momentum transmitter 27, any other type of distance-measuring device can be used, which generates a measuring pulse for each unit of distance traveled by the measuring platform 13.

Figure 3:
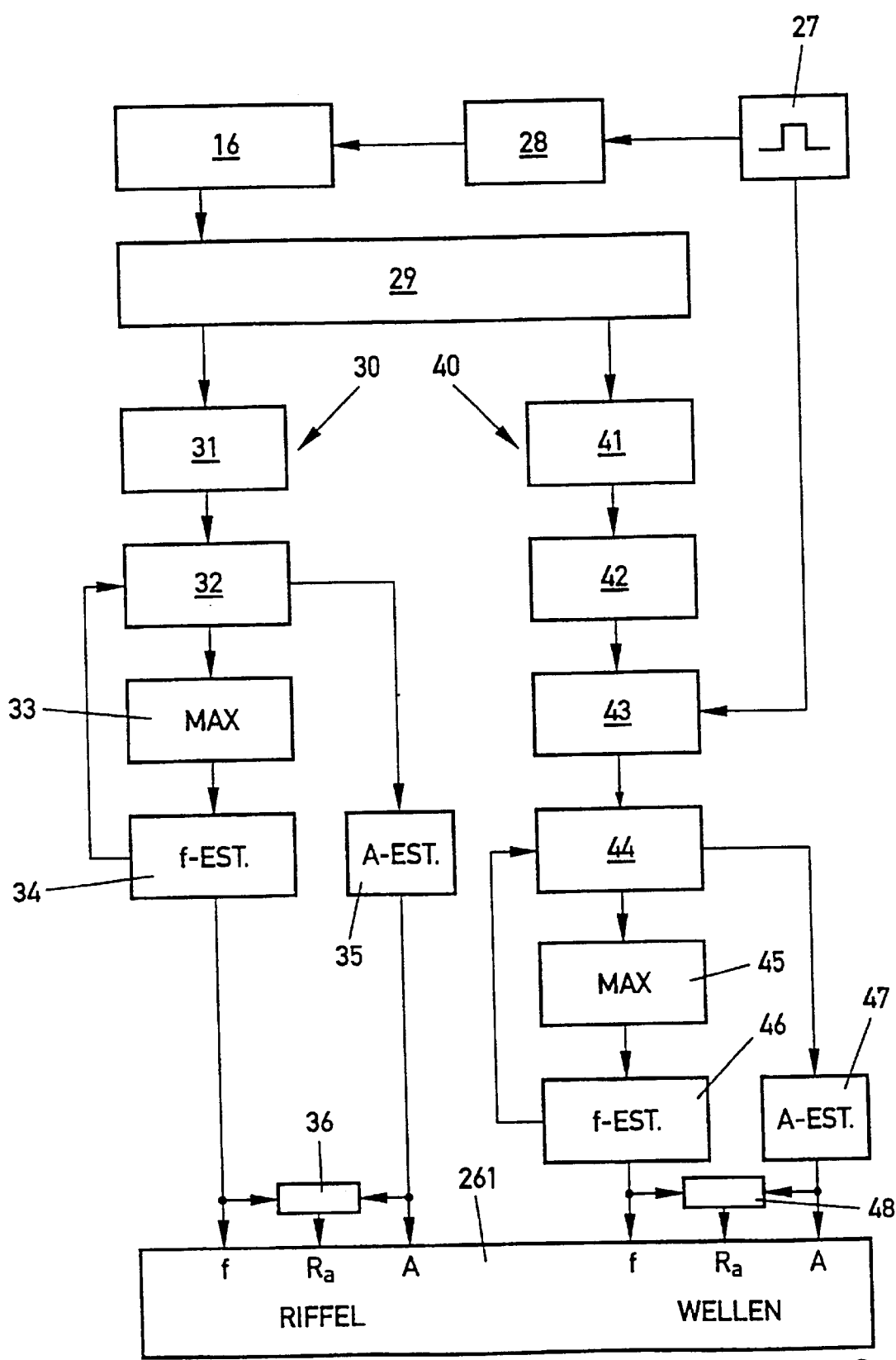
FIG. 3 is a block diagram of the measuring device according to FIGS. 1 and 2.

The evaluation of output signals provided by the camera for determining the driving surface unevenness occurs by means of a suitable signal processing method, which is performed by the hardware and software integrated in the PC 24. This signal processing method is described in the following with the aid of the block diagram for the measuring device, shown in FIG. 3. The signal processing is divided into the signal pre-processing that occurs in a signal pre-processing unit 29 and a signal processing for determining grooves and long waves. The result of the signal processing is shown on a display unit such as the monitor screen 261. In FIG. 3, a signal processing unit 30 for the grooves includes the signal processing units 31 to 36, and a signal processing unit 40 for the long waves comprises the signal processing units 41 to 48.

Figure 4:
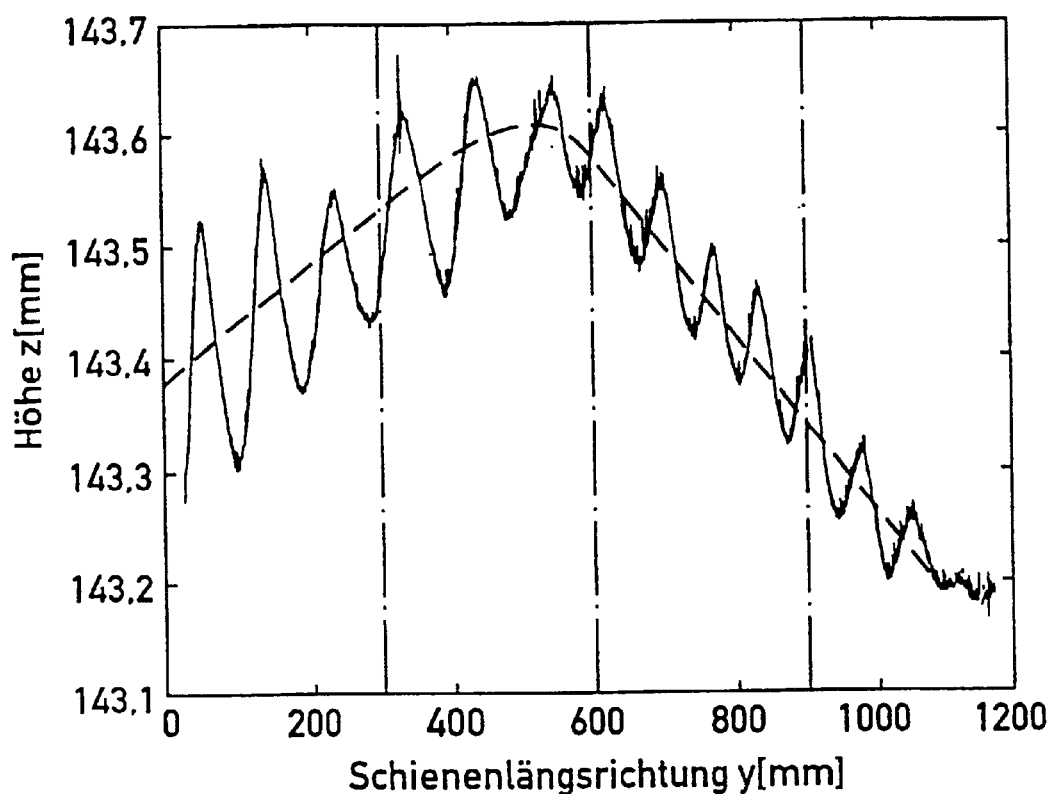
FIG. 4 is a detail of a light-section signal recorded by the measuring device.

A light-section signal is formed in the signal pre-processing unit 29 from each electric output signal of the photo receiver 18 of the camera 16, which is generated based on a light streak image. The light-section signal reflects the contour course of the light streak deformation over the length of the light streak in the light streak image. A light streak signal of this type is shown in FIG. 4 in sectional views for a scanned rail length of 1200 mm. The short-wave grooves are clearly visible and are superimposed on a long-wave surface deformation. If the rail length is scanned exactly and continuously with successive instantaneous exposures of camera 16, the signal segment shown in FIG. 4 results from the light streak images of four successive instantaneous exposures. More instantaneous exposures are required if the exposure ranges overlap, corresponding to the degree of overlapping. The signal pre-processing in the signal pre-processing unit 29 is preformed for each of the output signals supplied by the camera 16 for each instantaneous exposure.

A frequency analysis (DFT) is then performed for the light-section signal of each instantaneous exposure in the frequency-analysis unit 31 of signal processing unit 30 for grooves. Subsequently, the periodogram for the light-section signals is then formed from a square of the amount for complex values, obtained as follows. In a subsequent spectrum unit 32, a power density spectrum is estimated by means of incoherent averaging of a number of periodograms. In the process, the periodograms of, for example, eight light-section signals from successive instantaneous exposures are averaged. A maximum for the estimated power density spectrum is searched for in a maximum unit 33. An argument of the maximum is issued as a rough estimate of the groove frequency, which can be improved considerably in the frequency-estimation unit 34 with the aid of an estimation algorithm. The estimated groove frequency f is then supplied to the display unit and is shown numerically or graphically on the screen 261. At the same time, the value corresponding to this estimated frequency is read out of the spectrum unit 32 from the averaged periodograms or the estimated power density spectrum, and the amplitude for the grooves is determined from this in the amplitude-estimation unit 35. By assuming a sine-shaped course for grooves, it is easy to compute this amplitude from the frequency determined as double square root of the estimated power density spectrum. The amplitude A determined for grooves is shown on the screen 261. Following this, an arithmetic average rough value Ra for the driving surface 111 is computed, for example according to DIN 4768, from the estimated frequency and the groove amplitude and is displayed on the screen 261.

A coherent analysis is carried out in the signal-processing unit 40 to determine the long waves. The basic idea behind this signal processing is the determination of curvature values for the deformed light-section signals for each instantaneous exposure of the camera 16. Since the scanned moment of the rail segment with the light-section system 14 is known, a new signal can be synthesized from the plurality of curvature values, which contains information on the long waves. For this, each light-section signal, picked up at the output of the signal pre-processing unit 29, is subjected in a polynomial-adaptation unit 41 to a polynomial adaptation, preferably with the smallest-square method. The dashed line in FIG. 4 shows the result of such a polynomial adaptation in four successive light-section signals. With the estimated polynomial parameters, the curvature for each light-section signal is computed in a curvature computing unit 42. In a synthesizing unit 43, which is supplied with the timing of the instantaneous exposures derived from the angular moment transmitter 27, a measuring signal is then synthesized from the plurality of curvature values from successive instantaneous exposures, which measuring signal contains frequency and amplitude information for the long waves. Following a frequency analysis (DFT), the power density spectrum for the synthesized measuring signal is formed in a power density spectrum unit 44, which here corresponds to the periodogram for the synthesized measuring value signal. The maximum of the estimated power density spectrum is then searched for in a maximum unit 45, and the argument of the maximum as estimation for the frequency is used. An exact estimation of the frequency occurs in an estimation unit 46 by means of a suitable estimation algorithm. As for the signal processing unit 30 for grooves, the value belonging to the estimated frequency is determined from the estimated power density spectrum of the synthesized measuring signal and the amplitude for long waves is computed from this in unit 47. The roughness of the long waves is then determined from the frequency and amplitude estimate. The frequency f, the amplitude A and the arithmetic average rough value $R_a$ are then once more displayed on the screen 261. When computing the amplitude for long waves, it must be taken into account that these differ by one factor from the amplitude for the synthetic measuring signal (assuming a sine-shaped course).

The polynomial adaptation of a complete light-section signal for long waves with a wavelength λ of less than 500 mm does not lead to a satisfactory result. In that case, the light-section signals are divided into individual segments, each light-section signal segment is subjected to the above-described polynomial adaptation and the curvature is computed for each light-section signal segment. The curvature values are then combined in a corresponding manner to form a measuring signal.

Figure 5:
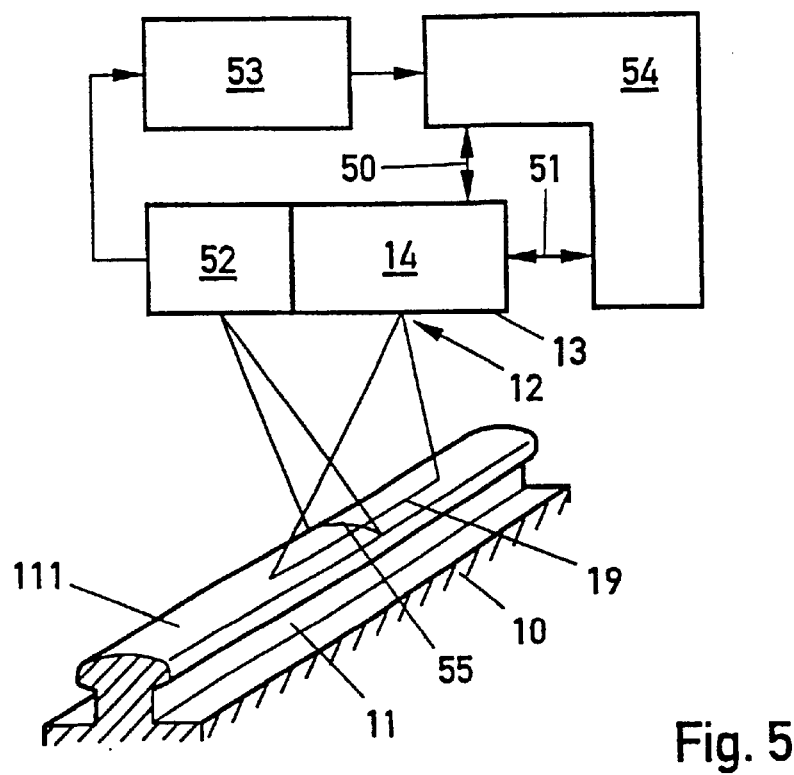
FIG. 5 shows an alternative embodiment of the invention with a modified measuring device.

For an exact measurement of the driving surface unevenness, it is necessary to perform the measurement at a fixed distance to the inside edge of the rails. Owing to vehicle movements, this can be ensured only with additional measures. Such measures are explained in the following in reference to FIG. 5. In FIG. 5, the light-section or laser triangulation system 14 arranged on the measuring platform 13 and the light streak 19 projected by its laser light source are shown. The measuring platform 13 in this case is positioned movably on the measuring cart in the cross-sectional profile plane of the rail 11, such that it can be moved relative to the rail in vertical direction (arrow 50) and crosswise to the rail in longitudinal direction (arrow 51). A position sensor arrangement 52 is additionally arranged on the measuring platform 13, the output signal of which is transmitted to a control computer 53. The control computer 53 is connected on the output side to a drive system 54, which can displace the measuring platform 13 in the direction of arrow 50 and/or in the direction of arrow 51 by predetermined path lengths. The position sensor arrangement 52 measures the cross-sectional railhead profile, which is used by the control computer 53 to determine the relative position of the light streak 19 in the cross-sectional profile and thus the position of measuring platform 13 relative to the rail 11. The control computer 53 then compares the distance between the light streak 19 and the inside edge of the rail to a predetermined desired value and, in case of a deviation of the actual value from the desired value, steers the drive system 54 until the difference reaches zero. A commercially available device for measuring the railhead cross-sectional profile can be used for the position sensor arrangement 52. In that case, the positioning occurs with the aid of an additional laser triangulation system, for which the measuring plane is turned by 90° relative to the laser triangulation system 14. The laser-light source for this system projects the laser streak with reference number 55 onto the rail 11, meaning at a right angle to the light streak 19. In that case, its recording camera does not require an anamorphotic lens and a 50 Hz measuring cycle is sufficient. The relative position of light streak 19, projected by the laser triangulation system 14 onto the driving surface 11 of the rail 11, is determined from the output signal of the recording camera and the measuring platform 13 is positioned with this signal.

According to an alternative embodiment, the measuring platform 13 does not have to be movable and mirrors can be arranged in the beam path of the laser light source with line optics and the camera 16, which mirrors are swiveled accordingly with the control signal from the control computer 53.

The invention is not limited to the described example for measuring unevenness on the driving surfaces of rails, for which a measuring cart supporting a measuring platform travels at an optional speed along the rails. The invention basically can be expanded to measuring the described unevenness on the surfaces of elongated or planar objects or items, wherein it does not matter whether the object or the measuring platform is moving. A possible use for the invention would be the measuring of the previously described unevenness on belts or sheet metal sheets that rest, for example, on a conveyor belt or are otherwise moved and in the process are transported past the stationary measuring platform. With planar objects such as sheet-metal sheets several measuring platforms are preferably arranged side-by-side for detecting the complete width of the sheet metal sheet. The advantage of the method and device according to the invention is that they are completely insensitive to vibrations or shaking of the measuring platform and/or the objects and that they permit a high measuring speed. Thus, the synchronization or the transporting means for transporting objects and articles past the measuring device do not have to meet high requirements.

What is claimed is:

1. A method for measuring unevenness formed by grooves and/or long waves in a surface of an object by using a measuring platform, comprising:

moving an object and a measuring platform relative to each other;

projecting from the measuring platform a light streak that extends in a direction of the movement onto the surface of the object at a fixed projection angle that is tilted relative to a normal to the surface;

reproducing the light streak on a planar, position-sensitive photo receiver with a plurality of successive instantaneous exposures of the photo receiver, where the photo receiver is fixedly arranged on the measuring platform with a recording angle that is tilted relative to the fixed projection angle;

recording the surface along the direction of the movement with a plurality of continuous light-streak images; and determining a surface profile of the surface along the direction of the movement from deformations in the plurality of the light-streak images.

2. A method according to claim 1, wherein a repetition rate for the plurality of successive instantaneous exposures is synchronized with a speed of the movement of the measuring platform and the object relative to each other.

3. A method according to claim 1, wherein a streak length of the light streak is longer than a wavelength of the grooves and smaller than a wavelength of the long waves.

4. A method according to claim 3, wherein a light-section signal, which reflects a curve course of deformation over the streak length of the light streak, is formed from an output signal of the photo receiver, which generates the output signal in response to receipt of a light-streak image.

5. A method according to claim 4, wherein in order to measure the grooves, the determining of the surface profile of the surface comprises forming periodograms of the light-section signal for each of the plurality of successive instantaneous exposures, and estimating a power density spectrum by means of an incoherent averaging of a number of periodograms.

6. A method according to claim 5, wherein the determining of the surface profile of the surface comprises searching for a maximum of an estimated power density spectrum and outputting an argument of the maximum as a rough estimation of a frequency of a groove.

7. A method according to claim 6, wherein the rough frequency estimation is improved by using an estimation algorithm.

8. A method according to claim 6, wherein the determining of the surface profile of the surface comprises determining an amplitude of the groove from a value of the estimated power-density spectrum, the value corresponding to the improved estimation of the frequency of the groove.

9. A method according to claim 4, wherein in order to measure the long waves in each instantaneous exposure, the determining of the surface profile of the surface comprises determining a curvature value of the light-section signal or curvature values of individual divided segments of the light-section signal and synthesizing a measuring signal from curvature values of the successive instantaneous exposures of the photo receiver, estimating a frequency and an amplitude of a long wave, and outputting the estimated frequency and amplitude.

10. A method according to claim 9, wherein the determining of the surface profile of the surface comprises subjecting the light-section signal or the individual divided segments of the light-section signal to a polynomial adaptation prior to the determining of the curvature value or the curvature values.

11. A method according to claim 9, wherein the determining of the surface profile of the surface comprises estimating a power-density spectrum from the synthesized measuring signal, searching for a maximum of the estimated power-density spectrum, using an argument of the maximum to estimate the frequency of the long wave.

12. A method according to claim 11, wherein the amplitude of the long wave is determined from a value of the estimated power-density spectrum, the value corresponding to the estimated frequency of the long wave.

13. A method according to claim 1, where the method is used for rails that are installed in a track bed for driving operations of rail traffic means, and where the measuring platform is driven along the rails and a driving surface of the rails forms the surface of the object.

14. A device, arranged on a measuring platform moving relative to rails, comprising:
a light-section or laser-triangulation system comprising:
a laser light source with line optics for projecting a light streak with a limited length and extending in a direction of the movement onto a driving surface of the rails; and
a surface camera with an optical axis that is tilted relative to an optical axis of the laser light source, where the surface camera is directed toward the driving surface and has a picture-taking sequence that is synchronized with a speed of the movement of the measuring platform relative to the rails;
a signal preprocessing unit;
a first signal processing unit connected to the signal pre-processing unit, the first signal processing unit estimating an amplitude and a frequency of grooves on the rails by means of incoherent averaging of a frequency spectrum of light-section signals, each light-section signal being formed from an output signal of a photo receiver of the surface camera, the photo receiver having the light streak reproduced on the photo receiver;
a second signal processing unit connected to the signal pre-processing unit for estimating an amplitude and a frequency of long waves on the rails by means of coherent analysis of the light-section signals;
a display unit for displaying and calculating amplitudes and frequencies of the grooves and long waves and the arithmetic average rough values of the driving surface of the rails, the arithmetic average rough values being determined from the calculated amplitudes and frequencies.

15. A device according to claim 14, wherein the surface camera is provided with an anamorphotic camera lens, where a linear magnification in a longitudinal direction of the rails is smaller than a linear magnification at a right angle thereto.

16. A device according to claim 14, wherein the measuring platform is arranged on a measuring cart that drives along the rails, a distance measuring device, which generates a measuring pulse for each path unit traveled by the measuring cart, is arranged on the measuring cart, and the measuring pulses are supplied to a synchronizing unit that controls the picture-taking sequence of the surface camera and to a second signal processing unit for the coherent analysis of the light-section signals.

17. A device according to claim 14, further comprising a position sensor arrangement that scans the driving surface of the rails in a lateral direction to the rails, a control device connected to the position sensor arrangement, the control device controlling the light-section or laser triangulation system based on an output signal from the position sensor arrangement so that the light streak projected by the light-section or laser triangulation system onto the driving surface is at a constant distance laterally to the inside edge of the rails.

18. A device according to claim 17, further comprising a control computer having an input connected to the position sensor arrangement, wherein the measuring platform has an adjustable position on the measuring cart in a profile plane of the rails, and wherein the control device is provided with a drive that adjusts the measuring platform in a vertical direction in the profile plane and further adjusts the measuring platform in a lateral direction in the profile plane, where the control computer controls the drive.

19. A method according to claim 1, wherein longitudinal segments of the continuous light-streak images have overlaps in the direction of the movement.

20. A method according to claim 1, wherein a streak length of the light streak is in the order of magnitude of 300 mm and 500 mm.

21. A method according to claim 8, wherein the amplitude of the groove is computed as a double square root of the estimated power-density spectrum.

22. A method according to claim 10, wherein in the subjecting of the light-section signal or the individual divided segments of the light-section signal to a polynomial adaptation, a smallest square method is used.

23. A method according to claim 16, wherein the distance measuring device is an angular momentum transmitter that emits a fixed number of pulses for each rotation of a wheel on the measuring cart.

* * * * *